(12) United States Patent
Panzani et al.

(10) Patent No.: US 7,001,323 B2
(45) Date of Patent: *Feb. 21, 2006

(54) METHOD FOR CONTROLLING THE WASHING STEP IN A BLOOD CENTRIFUGATION CELL

(75) Inventors: Ivo Panzani, Mirandola (IT); Sergio Romagnoli, Castenaso (IT); Massimo Belloni, Isola Della Scala (IT)

(73) Assignee: Dideco S.r.l., Mirandola (IT)

(*) Notice: Subject to any disclaimer, the term of this patent is extended or adjusted under 35 U.S.C. 154(b) by 0 days.

This patent is subject to a terminal disclaimer.

(21) Appl. No.: 10/805,086

(22) Filed: Mar. 19, 2004

(65) Prior Publication Data
US 2004/0173540 A1 Sep. 9, 2004

Related U.S. Application Data

(63) Continuation of application No. 10/125,995, filed on Apr. 19, 2002, now Pat. No. 6,716,151.

(30) Foreign Application Priority Data
Apr. 30, 2001 (IT) .......................... MI2001A0899

(51) Int. Cl.
*B04B 13/00* (2006.01)

(52) U.S. Cl. .......................... 494/37; 210/739; 210/787
(58) Field of Classification Search ................ 494/1, 494/5–6, 10–11, 37, 41, 42, 43, 45; 604/4.01, 604/5.01, 6.11; 210/104, 143, 782, 787, 210/87, 96.1, 739
See application file for complete search history.

(56) References Cited

U.S. PATENT DOCUMENTS

| | | | |
|---|---|---|---|
| 4,919,817 A | 4/1990 | Schoendorfer et al. |
| 5,298,171 A | 3/1994 | Biesel |
| 5,311,908 A | 5/1994 | Barone et al. |
| 5,379,775 A | 1/1995 | Kruse |
| 5,383,911 A | 1/1995 | Mann |
| 5,385,539 A | 1/1995 | Maynard |

(Continued)

FOREIGN PATENT DOCUMENTS

EP 0 682 953 A1 11/1995

(Continued)

OTHER PUBLICATIONS

Gilbert et al., "Hematocrit Monitor," *Critical Care Medicine*, 17(9):929-933 (Sep. 1989).

(Continued)

*Primary Examiner*—Charles E. Cooley
(74) *Attorney, Agent, or Firm*—Popovich, Wiles & O'Connell, P.A.

(57) ABSTRACT

A method and apparatus for controlling the washing step in a blood centrifugation cell in which washing solution is introduced into the blood centrifugation cell and the cell contains compacted red cells and supernatant at the beginning of the washing step. The apparatus can comprise various sensors and a computer. The sensors sense and transmit to the computer three inputs. The first input is indicative of the total volume of blood that enters the cell during the filling step and the total amount of washing solution that enters the cell during the washing step. The second input is indicative of the hematocrit value of the blood introduced during the filling step. The third input is indicative of the geometric characteristics of the cell. Based on the inputs, the computer executes an algorithm that produces a first output that is the concentration of the supernatant in the supernatant-washing solution mixture.

17 Claims, 1 Drawing Sheet

U.S. PATENT DOCUMENTS

| | | | |
|---|---|---|---|
| 5,387,174 A | 2/1995 | Rochat | |
| 5,417,715 A | 5/1995 | Noren et al. | |
| 5,423,738 A | 6/1995 | Robinson et al. | |
| 5,607,579 A | 3/1997 | Latham, Jr. et al. | |
| 5,730,883 A | 3/1998 | Brown | |
| 5,876,611 A | 3/1999 | Shettigar | |
| 5,919,125 A | 7/1999 | Berch | |
| 6,241,649 B1 | 6/2001 | Zanella et al. | |
| 6,299,784 B1 | 10/2001 | Biesel | |
| 6,352,499 B1 * | 3/2002 | Geigle | 494/37 |
| 6,416,456 B1 * | 7/2002 | Zanella et al. | 494/37 |
| 6,605,028 B1 | 8/2003 | Dolecek | |
| 6,629,919 B1 * | 10/2003 | Egozy et al. | 494/37 |
| 6,716,151 B1 * | 4/2004 | Panzani et al. | 494/10 |
| 2003/0181305 A1 * | 9/2003 | Briggs et al. | 494/37 |
| 2005/0054508 A1 * | 3/2005 | Panzani et al. | 210/787 |

FOREIGN PATENT DOCUMENTS

| | | |
|---|---|---|
| EP | 0 931 554 A2 | 7/1999 |
| EP | 0 931 554 A3 | 7/1999 |
| EP | 1254675 * | 11/2005 |
| WO | WO 98/29149 | 7/1998 |

OTHER PUBLICATIONS

Steinke et al., "Role of Light Scattering in Whole Blood Oximetry," *IEEE Transactions on Biomedical Engineering*, BME-33(3):294-301 (Mar. 1986).

Zdrojkowski et al., "Optical Transmission and Reflection by Blood," *IEEE Transactions on Biomedical Engineering*, BME-17(2):122-128 (Apr. 1970).

US 6,348,030, 02/2002, Zanella et al. (withdrawn)

* cited by examiner

METHOD FOR CONTROLLING THE WASHING STEP IN A BLOOD CENTRIFUGATION CELL

This application is a continuation of U.S. Ser. No. 10/125,995, filed Apr. 19, 2002, now U.S. Pat. No. 6,716,151 issued Apr. 6, 2004, the contents of which are hereby incorporated by reference herein.

FIELD OF THE INVENTION

The invention relates to blood centrifuges and in particular relates to a system for controlling the washing step in a blood centrifugation cell.

BACKGROUND OF THE INVENTION

It is known that in some medical procedures, such as inter- and post-operative autotransfusion, there is the need to separate the plasma from the red cells of the blood aspirated from the operating area, so as to make them available for re-infusion to the patient. It is also known that currently this procedure is performed in centrifugation cells in which the blood is introduced by means of a peristaltic pump.

A centrifugation cell substantially comprises two bells which are mutually coaxial and rigidly coupled, and the portion of space between them is connected to the outside by means of two tubes, an inlet tube and an outlet tube, which are connected to the bells by means of a rotary coupling. The two bells are turned about their own axis, while the tubes are kept motionless.

The procedure provides for a first step for filling the cell, in which the blood is introduced by means of the inlet tube. Due to the centrifugal force, the red cells, which are the heaviest cellular components of blood, are propelled outward, compacting against the wall of the outer bell. Other cellular components such as white blood cells and platelets are arranged in a thin layer known as buffy coat directly adjacent to the mass of compacted red blood cells. The separated plasma, the remaining component of blood, is arranged in a layer which lies above the buffy coat. The plasma, which contains various substances such as anticoagulant, free hemoglobin and other substances from the operating field, will be referenced hereinafter as "supernatant".

As filling continues, the buffy coat moves closer to the rotation axis, displacing the supernatant toward the outlet tube of the cell. When the supernatant reaches the outlet tube the supernatant flows out of the cell into an adapted collection bag.

The flow of the supernatant in the outlet tube continues until an optical detector reports that the buffy coat has reached the outlet tube of the cell. At this point the filling step has ended and the introduction of new blood into the cell ends. The cell now contains compacted red cells and supernatant, which must be eliminated since it cannot be re-infused to the patient together with the red cells.

The above-described filling step is followed by a washing step performed by means of a washing solution which, when introduced into the cell, gradually takes the place of the supernatant that is expelled. At the end of the washing step the cell contains red cells and washing solution, i.e., substances suitable to be re-infused to the patient. The contents of the cell are collected in a suitable bag in a third step of the procedure, known as emptying.

Our attention is focused exclusively on the washing step, which is currently performed in manners that are not entirely satisfactory. A first procedure adopted in the background art provides for introducing in the cell a preset amount of washing solution at a value that is assuredly more than sufficient to wash the supernatant. The consequent oversizing, however, wastes time and washing solution.

Another procedure used in the art provides a transparency sensor on the outlet duct. However, this sensor is not able to detect the passage of transparent components of the supernatant such as the anticoagulant, and therefore does not provide entirely satisfactory results.

SUMMARY OF THE INVENTION

The invention provides a system for controlling the washing step in which the washing step can be stopped when the intended result is reached. The present invention provides a method for controlling a washing step in a blood centrifugation cell wherein washing solution is introduced into the blood centrifugation cell in the washing step, the cell containing compacted red blood cells and supernatant at the beginning of the washing step. The method comprises: (1) providing a blood centrifugation cell, a pump for communicating liquid to the blood centrifugation cell, and a computer configured to receive data and produce at least one output; (2) providing first input data to the computer indicative of the total volume of liquid that has entered the cell during the filling step that precedes the washing step and during the washing step itself, the liquid being blood during the filling step and the liquid being washing solution during the washing step; (3) providing second input data to the computer indicative of the hematocrit value of the blood that was introduced during the filling step; (4) providing third input data to the computer indicative of the geometric characteristics of the cell; (5) processing the first, second, and third input data in the computer to produce a first output, said first output being the concentration of the supernatant in the supernatant-washing solution mixture that is present in the cell during the washing step, said first output being produced by the computer executing an algorithm that expresses the supernatant extinction law inside the cell using the first, second, and third input data; and (6) stopping the washing step when a certain concentration of supernatant in the supernatant-washing solution is reached.

In addition, the invention provides an apparatus for performing the method for controlling the washing step in a blood centrifugation cell.

DETAILED DESCRIPTION OF THE PREFERRED EMBODIMENTS

Figure 2:
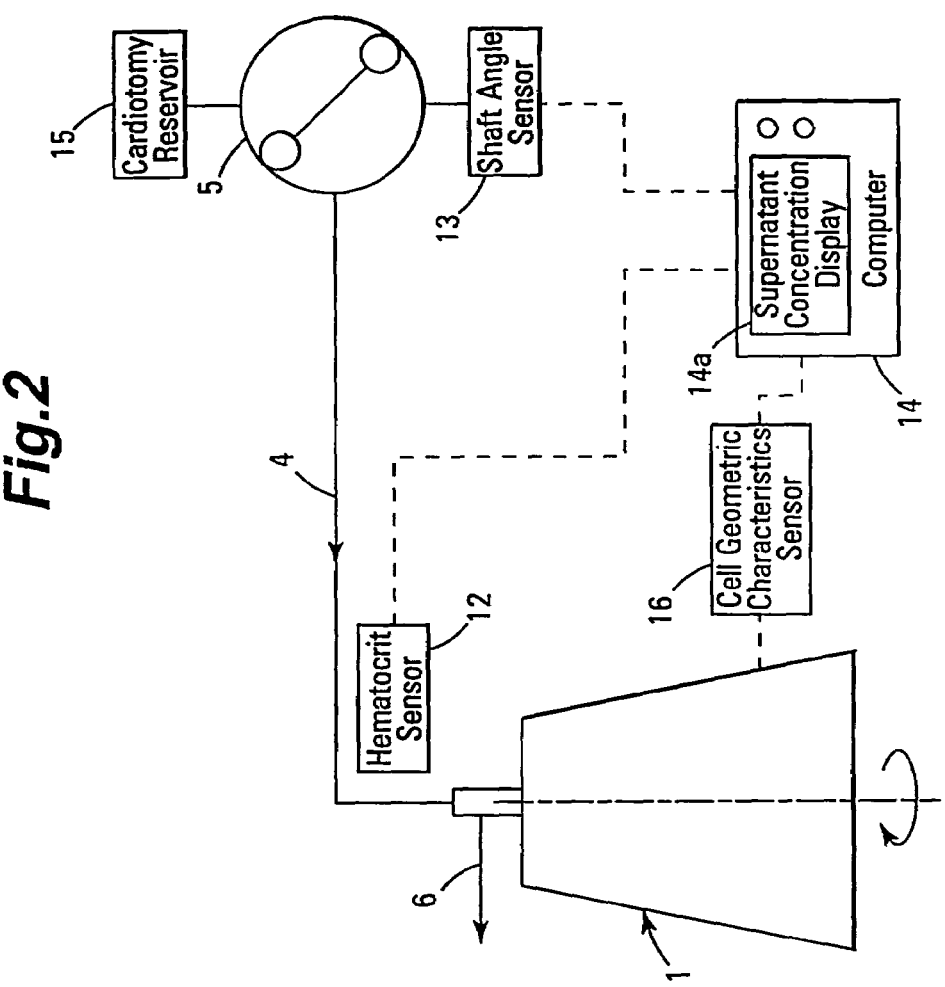
FIG. 2 is a diagram of an apparatus of the invention.
Figure 1:
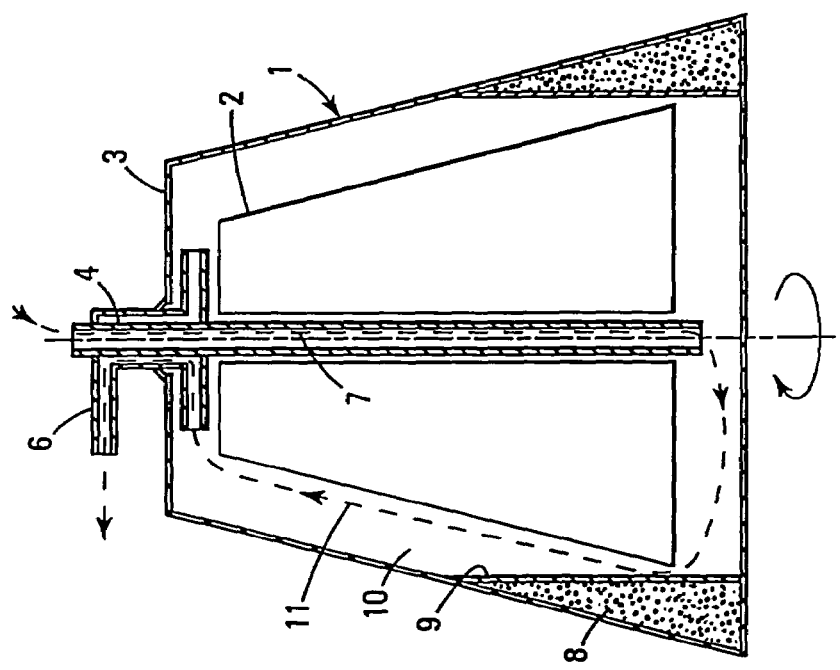
FIG. 1 is a schematic view of a blood centrifugation cell.

With reference to the figures, the reference numeral 1 generally designates the blood centrifugation cell, which comprises inner bell 2 and outer bell 3, which are mutually rigidly coupled and are made to rotate in the direction of the arrow in the figures. The numeral 4 respectively designates the inlet tube to the portion of space comprised between the two bells. Peristaltic pump 5 pumps fluids into inlet tube 4. The fluids follow path 7 into region 10 between the inner and outer bells. Centrifugation separates blood components, as described further below, and supernatant flows out of the centrifuge via outlet tube 6. The inlet and outlet tubes are connected to the assembly of the inner and outer bells by means of a rotary coupling, so that they can remain motionless.

During the cell filling step, the red blood cells enter the cell along path 7 due to the action of the peristaltic pump 5, which is connected at the suction to a container known as a cardiotomy reservoir 15. During centrifugation, the red blood cells are compacted in region 8, and the supernatant follows path 11 to the outlet tube 6. Buffy coat 9 separates the compacted red blood cells from the supernatant in region 10. The supernatant then flows toward the outlet tube 6 of the cell along the path 11.

When buffy coat 9, by moving increasingly closer to the rotation axis, reaches the full level indicated by a sensor, the introduction of blood into the cell ceases as pump 5 stops. Now the filling step has ended and cell 1 contains compacted red cells and supernatant.

This is followed by a washing step to eliminate the supernatant by means of a washing solution. A preferred washing solution is physiological saline solution (0.9 g/L NaCl in water). The washing solution is conveyed to cell 1 through inlet tube 4 by pump 5, which is in communication with a reservoir of washing solution.

The washing solution gradually takes the place of the supernatant, and at the end of the washing step in cell 1, the replacement of the supernatant with the washing solution has occurred substantially completely. A minute amount of supernatant in cell 1 remains and will be reinfused to the patient. However, small amounts of supernatant are obviously tolerable.

During the washing step, therefore, in the volume of the cell 1 that is not occupied by the compacted red cells, there is a mixture of supernatant and washing solution. The expression "supernatant concentration" is used to designate the ratio between the volume of supernatant present in said mixture and the total volume of said mixture, and it is immediately evident that the value of said concentration varies during washing from the initial value of 1, when all the space available is occupied by the supernatant, toward the ideal final value, which is zero and would be reached if the supernatant were eliminated completely and fully replaced by the washing solution. The expression "supernatant extinction law" is used to designate the law that regulates the variation of the concentration of supernatant in the supernatant-washing solution mixture as it decreases from the initial value of 1 toward the final value.

The control system includes sensor 12, which is suitable to provide the hematocrit reading of the blood entering the cell during the filling step, encoder or sensor 13 on the driving shaft of the peristaltic pump 5, which detects data related to the rotation angles of said shaft, and computer 14.

The computer executes an algorithm, derived from a mathematical model or from the processing of experimental data, that expresses the supernatant extinction law within cell 1 and has three inputs and one output.

The first input comprises the volume of the liquid that enters the cell during the filling step, which is blood, and during the washing step, which is washing solution. This first input is provided, in the described embodiment, by the encoder 13. The data it transmits to the computer 14 related to the rotation angles gradually covered by the pump 5 are converted, since the characteristics of said pump and of the tube 4 are known, into data related to the volume of liquid progressively conveyed. However, clearly the encoder 13 might be replaced with any liquid flow measurement instrument.

The second input comprises the hematocrit reading of the blood entering cell 1 during the filling step, and is provided by sensor 12, which reports to computer 14 the hematocrit reading of the individual small volumes of blood that enter cell 1 continuously. The second input might be provided in other forms. For example, the computer 14 could include an operator interface which allows entering into the computer 14 data related to the hematocrit value of the blood, which can be determined from the cardiotomy reservoir located at the intake of the pump 5.

The third input comprises the geometric characteristics of the cell. Accordingly, there are means that allow the operator to enter into computer 14 data related to these characteristics. Alternatively, a sensor 16 could be provided for automatic detection of said characteristics.

On the basis of the three listed inputs, computer 14 provides an output at each instant of the value of the concentration of supernatant in the supernatant-washing solution mixture that is present in the cell 1 during the washing step. In addition, it is possible to provide time as a fourth input.

The invention includes means that allow stopping the washing step when the intended conditions are reached. In the described embodiment there is the display 14a, which shows at each instant the value of the concentration of supernatant and thus allows the operator to intervene and turn off the pump 5 when said value reaches the threshold deemed acceptable. According to a different embodiment, there is a controller to stop automatically the operation of the pump 5 when said concentration reaches the threshold value that is preset as acceptable.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for centrifuging blood in a filling step and controlling a washing step in a blood centrifugation cell wherein blood is introduced into the blood centrifugation cell in the filling step and washing solution is introduced into the blood centrifugation cell in the washing step, the method comprising:

providing a blood centrifugation cell, a pump for communicating liquid to the blood centrifugation cell, and a computer configured to receive data and produce at least one output;

introducing blood into the blood centrifugation cell during the filling step;

centrifuging the blood so the cell contains compacted red blood cells and supernatant at the beginning of the washing step, providing first input data to the computer indicative of the total volume of liquid that has entered the cell during the filling step that precedes the washing step and during the washing step itself, the liquid being blood during the filling step and the liquid being washing solution during the washing step;

providing second input data to the computer indicative of the hematocrit value of the blood that was introduced during the filling step;

providing third input data to the computer indicative of the geometric characteristics of the cell;

processing the first, second, and third input data in the computer to produce a first output, said first output being the concentration of the supernatant in the supernatant-washing solution mixture that is present in the cell during the washing step, said first output being produced by the computer executing an algorithm that expresses the supernatant extinction law inside the cell using the first, second, and third input data; and stopping the washing step when a certain concentration of supernatant in the supernatant-washing solution is reached.

2. The method of claim 1, wherein the algorithm has time as a fourth input data.

3. The method of claim 1, wherein the algorithm that expresses the supernatant extinction law inside the cell is derived from a mathematical model.

4. The method of claim 1, wherein the algorithm that expresses the supernatant extinction law inside the cell is derived from an experimental analysis.

5. The method of claim 1, wherein the pump is a peristaltic pump comprising on the drive shaft of the pump a sensor suitable to transmit to the computer said first input data related to the rotation angles of said drive shaft.

6. The method of claim 1, further comprising providing a sensor for measuring the volume of liquid entering the cell and suitable to transmit to the computer said first input data.

7. The method of claim 1, further comprising providing a sensor for measuring the hematocrit value of the blood entering the cell during the filling step and suitable to transmit to the computer said second input data.

8. The method of claim 1, further comprising providing an operator interface for entering into the computer said second input data indicative of the hematocrit value of the blood.

9. The method of claim 8, wherein said pump comprises an intake and a cardiotomy reservoir is located at the intake for said pump, and wherein said data indicative of the hematocrit value of the blood is determined by measuring a hematocrit value of the blood in the cardiotomy reservoir.

10. The method of claim 1, further comprising providing an operator interface for entering into the computer said third input data indicative of the geometric characteristics of the cell.

11. The method of claim 1, further comprising providing a sensor for automatically detecting the geometric characteristics of the cell and suitable to transmit to the computer said third input data.

12. The method of claim 1, further comprising providing an operator interface for displaying the concentration of the supernatant in the supernatant-washing solution mixture.

13. The method of claim 12, wherein the operator stops the washing step when a certain concentration of supernatant is reached.

14. The method of claim 1, further comprising providing a controller for stopping the washing step when a certain concentration of supernatant in the supernatant-washing solution is reached.

15. The method of claim 14, wherein the controller stops the washing step when a preset value of the concentration of supernatant in the supernatant-washing solution mixture is reached.

16. A method for centrifuging blood in a filling step and controlling a washing step in a blood centrifugation cell wherein blood is introduced into the blood centrifugation cell in the filling step and washing solution is introduced into the blood centrifugation cell in the washing step, the method comprising:

providing a blood centrifugation cell, a pump for communicating liquid to the blood centrifugation cell, and a computer configured to receive data and produce at least one output;

introducing blood into the blood centrifugation cell during the filling step;

centrifuging the blood so the cell contains compacted red blood cells and supernatant at the beginning of the washing step;

providing first input data to the computer indicative of the total volume of liquid that has entered the cell during the filling step that precedes the washing step and during the washing step itself, the liquid being blood during the filling step and the liquid being washing solution during the washing step;

providing second input data to the computer indicative of the hematocrit value of the blood tat was introduced during the filling step;

providing third input data to the computer indicative of the geometric characteristics of the cell; and processing the first, second, and third input data in the computer to produce a first output said first output being the concentration of the supernatant in the supernatant-washing solution mixture that is present in the cell during the washing step, said first output being produced by the computer executing an algorithm that expresses the supernatant extinction law inside the cell using the first, second, and third input data.

17. A method for controlling a washing step in a blood centrifugation cell wherein washing solution is introduced into the blood centrifugation cell in the washing step, the method comprising;

providing a blood centrifugation cell, a pump for communicating liquid to the blood centrifugation cell, and a computer configured to receive data and produce at least one output;

providing first input data to the computer indicative of the total volume of liquid that has entered the cell during the filling step that precedes the washing step and during the washing step itself, the liquid being blood during the filling step and the liquid being washing solution during the washing step;

providing second input data to the computer indicative of the hematocrit value of the blood that was introduced during the filling step;

providing third input data to the computer indicative of the geometric characteristics of the cell; and processing the first, second, and third input data in the computer to produce a first output, said first output being the concentration of the supernatant in the supernatant-washing solution mixture that is present in the cell during the washing step, said first output being produced by the computer executing an algorithm that expresses the supernatant extinction law inside the cell using the first, second, and third input data.

* * * * *